United States Patent
Bippus et al.

(10) Patent No.: US 10,213,167 B2
(45) Date of Patent: Feb. 26, 2019

(54) CONTRAST AGENT DOSE SIMULATION

(71) Applicant: KONINKLIJKE PHILIPS N.V., Eindhoven (NL)

(72) Inventors: Rolf Dieter Bippus, Hamburg (DE); Thomas Koehler, Norderstedt (DE); Michael Grass, Buchholz in der Nordheide (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 35 days.

(21) Appl. No.: 15/316,540

(22) PCT Filed: May 26, 2015

(86) PCT No.: PCT/IB2015/053917
§ 371 (c)(1),
(2) Date: Dec. 6, 2016

(87) PCT Pub. No.: WO2015/189730
PCT Pub. Date: Dec. 17, 2015

(65) Prior Publication Data
US 2017/0181714 A1    Jun. 29, 2017

Related U.S. Application Data

(60) Provisional application No. 62/011,110, filed on Jun. 12, 2014.

(51) Int. Cl.
*A61B 6/00* (2006.01)
*G06T 11/00* (2006.01)
*A61B 6/03* (2006.01)

(52) U.S. Cl.
CPC ............. *A61B 6/032* (2013.01); *A61B 6/481* (2013.01); *A61B 6/482* (2013.01); *A61B 6/5205* (2013.01);
(Continued)

(58) Field of Classification Search
CPC .............. A61B 6/481; G06T 11/005; G06T 2207/10081; G06T 2211/408; G06T 11/008
See application file for complete search history.

(56) References Cited

U.S. PATENT DOCUMENTS

| 8,442,184 | B2 | 5/2013 | Forthmann |
| 2003/0031299 | A1* | 2/2003 | Ohishi ................... A61B 6/481 378/162 |

(Continued)

FOREIGN PATENT DOCUMENTS

| WO | 1997/025923 | 7/1997 |
| WO | 2009/109887 | 9/2009 |
| WO | 2013/011418 | 1/2013 |

OTHER PUBLICATIONS

Muddah, et al., "Physically meaningful virtual unenhanced image reconstruction from dual-energy CT" Biomedical Imaging: From Nano to Macro, 2010 IEEE International Symposium.

(Continued)

Primary Examiner — Utpal D Shah

(57) ABSTRACT

A method includes obtaining a set of energy dependent data generated from a spectral scan. The set of energy dependent data includes a sub-set of data corresponding to only contrast agent. The method further includes separating the sub-set of data from other data of the energy dependent data. The other data includes non-contrast agent data. The method further includes scaling the sub-set of data to change a concentration of the contrast agent in the sub-set of data from that of the sub-set of data. The method further includes visually presenting at least the scaled sub-set of data.

19 Claims, 5 Drawing Sheets

(52) U.S. Cl.
CPC .......... *G06T 11/005* (2013.01); *G06T 11/008* (2013.01); *A61B 6/48* (2013.01); *A61B 6/52* (2013.01); *G06T 11/003* (2013.01); *G06T 2211/408* (2013.01)

(56) References Cited

U.S. PATENT DOCUMENTS

| | | | |
|---|---|---|---|
| 2008/0253634 A1 | 10/2008 | Hay | |
| 2009/0074277 A1* | 3/2009 | Deinzer | G06T 7/33 |
| | | | 382/130 |
| 2009/0080749 A1* | 3/2009 | Visser | G06T 3/4007 |
| | | | 382/131 |
| 2010/0166273 A1* | 7/2010 | Wismuller | G06T 7/0012 |
| | | | 382/131 |
| 2011/0245675 A1* | 10/2011 | Yoshida | A61B 8/461 |
| | | | 600/443 |
| 2013/0261441 A1 | 10/2013 | Das | |
| 2013/0324845 A1 | 12/2013 | Korporaal | |
| 2015/0003591 A1* | 1/2015 | Schweizer | A61B 6/481 |
| | | | 378/62 |

OTHER PUBLICATIONS

Li, et al., "Simultaneous Reduction in Noise and Cross-Contamination Artifacts for Dual-Energy X-Ray CT", Biomed Research International, vol. 174, No. 1, 2013.
Kalender, et al., "Application- and patient size-dependent optimization of x-ray spectra for CT" Med. Phys. 36 (3) Mar. 2009.
ACR Manual on Contrast Media, Version 9, 2013.

* cited by examiner

CONTRAST AGENT DOSE SIMULATION

CROSS REFERENCE TO RELATED APPLICATIONS

This application is the U.S. National Phase application under 35 U.S.C. § 371 of International Application No. PCT/IB2015/053917, filed May 26, 2015, published as WO 2015/189730 on Dec. 17, 2015, which claims the benefit of U.S. Provisional Patent Application No. 62/011,110, filed on Jun. 12, 2014. These applications are hereby incorporated by reference herein.

The following generally relates to simulating a contrast enhanced image based on projection and/or image data from a contrast enhanced scan, and is described with particular application to computed tomography (CT). However, the following is also amenable to other imaging applications, such as X-ray, C-Arm volume imaging, breast tomosynthesis, and/or other imaging.

Spectral (or multi-energy) CT utilizes multiple attenuation values acquired simultaneously at multiple different photon energies to solve for photoelectric effect, Compton scattering, and other component(s) (e.g., K-edge) contributions of the mass attenuation coefficient of a material. There are several approaches to perform multiple energy CT acquisitions such as using multiple x-ray tubes, kVp switching, multi-layer detectors, and photon counting detectors.

Contrast-enhanced scans require administration of a contrast agent. The literature indicates that various forms of contrast media have been used to improve medical imaging and that their value has long been recognized, as attested to by their common daily use in imaging departments worldwide. However, like other pharmaceuticals, such agents are not completely devoid of risk. As such, the amount of contrast agent administered is a critical, limiting factor due to the possibility of adverse effects on the patient.

For example, according to the ACR Manual on Contrast Media, Version 9, 2013, adverse side effects from the administration of contrast media vary from minor physiological disturbances to rare severe life-threatening situations. Thus, contrast dose should be kept low. Unfortunately, the optimization of scanning protocols is often limited since the diagnostic value of a scan should not be compromised, and, in current clinical settings, doses are kept quite high to assure sufficient visibility of the vascular anatomy or contrast agent uptake in the tissue.

Aspects described herein address the above-referenced problems and others.

The following describes an approach to retrospectively simulate (or create a virtual) image from existing data corresponding to a previously acquired contrast enhanced data set in which the simulated or virtual image has less contrast agent than the existing contrast enhanced data set. This can be achieved in the projection and/or image domain by scaling the contrast agent only data and generating the image from the scaled contrast agent only data and/or a combination of the scaled contrast agent only data with non-scaled non-contrast agent data.

In one aspect, a method includes obtaining a set of energy dependent data generated from a spectral scan. The set of energy dependent data includes a sub-set of data corresponding to only contrast agent. The method further includes separating the sub-set of data from other data of the energy dependent data. The other data includes non-contrast agent data. The method further includes scaling the sub-set of data to change a concentration of the contrast agent in the sub-set of data from that of the sub-set of data. The method further includes visually presenting at least the scaled sub-set of data.

In another aspect, a computing system includes a memory that stores instructions for a contrast agent concentration simulation module, and a processor that receives a set of energy dependent data, including a first sub-set of data corresponding to only contrast agent and second sub-set of data corresponding to only non-contrast agent; extracts the first sub-set of data corresponding to only contrast agent; changes a concentration of the contrast agent in the extracted first sub-set of data corresponding to only contrast agent; and visually presents at least the changed concentration sub-set of data.

In another aspect, a computer readable storage medium is encoded with computer readable instructions. The computer readable instructions, when executed by a processer, causes the processor to: generate a virtual image with a contrast agent concentration that is less than an administered contrast agent concentration based on scan data from a scan with the administered contrast agent concentration.

The invention may take form in various components and arrangements of components, and in various steps and arrangements of steps. The drawings are only for purposes of illustrating the preferred embodiments and are not to be construed as limiting the invention.

FIG. 1 schematically illustrates an example computing system, with a contrast agent dose simulation module, in connection with an imaging system.

FIG. 2 schematically illustrates an example of the contrast agent dose simulation module, which includes a projection domain processor and an image domain processor.

FIG. 3 schematically illustrates an example of the projection domain processor of the contrast agent dose simulation module.

FIG. 4 schematically illustrates an example of the image domain processor of the contrast agent dose simulation module.

Figure 1:
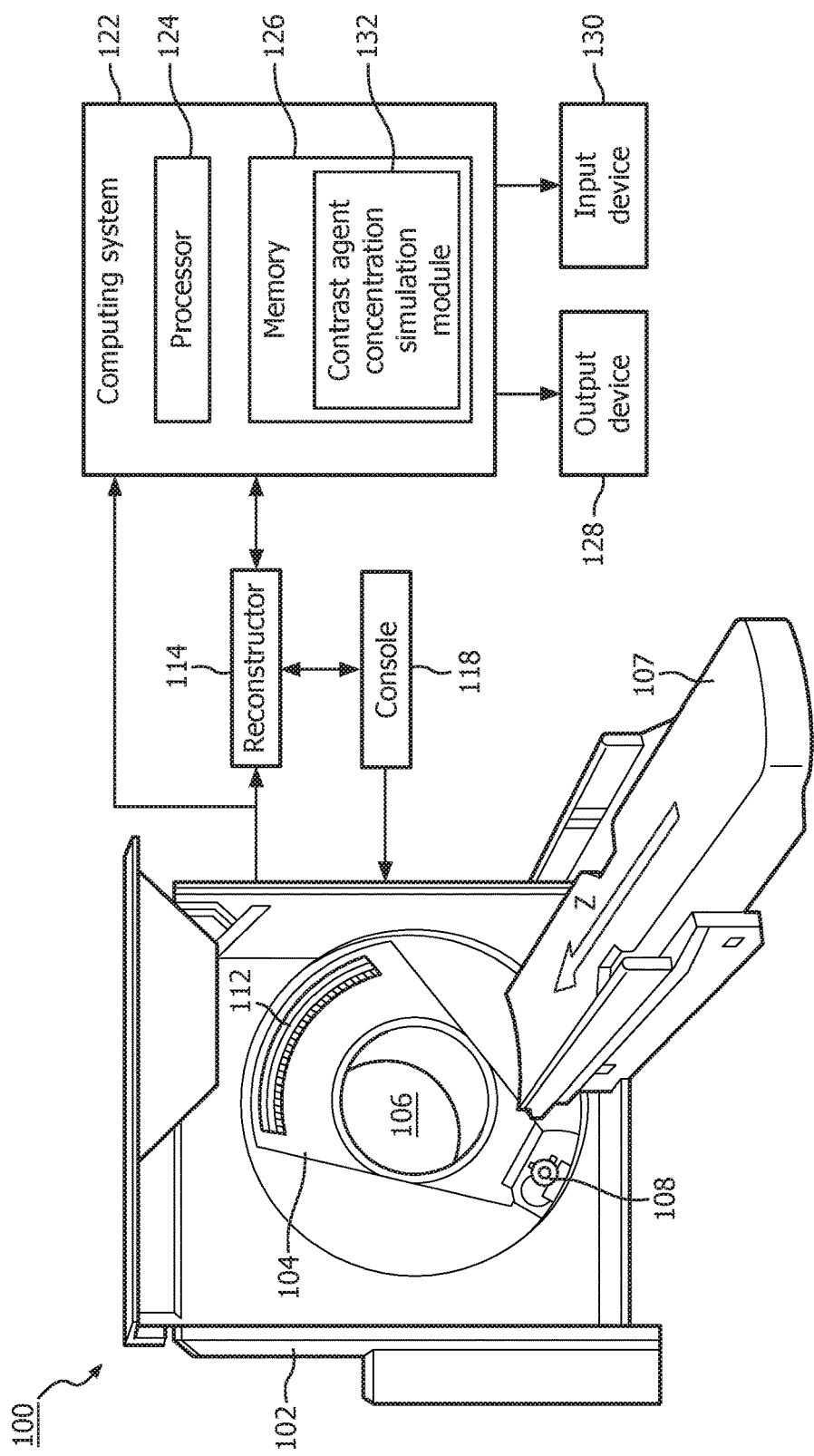

Initially referring to FIG. 1, an imaging system 100, such as a computed tomography (CT) scanner, is illustrated. The imaging system 100 includes a generally stationary gantry 102 and a rotating gantry 104, which is rotatably supported by the stationary gantry 102 and rotates around an examination region 106 about a z-axis. A subject support 107 such as a couch supports a subject or object in the examination region 106. The subject support 107 is movable in coordination with scanning so as to guide the subject or object with respect to the examination region 106 for scan of the subject or object.

A radiation source 108, such as an x-ray tube, is rotatably supported by the rotating gantry 104, rotates with the rotating gantry 104, and emits radiation that traverses the examination region 106. In one instance, a controller controls a mean or peak emission voltage of the radiation source 108. This includes switching the emission voltage between two or more emission voltages (e.g., 80 and 140 kVp, 100 and 120 kVp, etc.) within an integration period and/or otherwise. In a variation, the imaging system 100 includes at least two radiation sources 108 that emit radiation at different emission voltages. In another variation, the radiation source 108 includes a single broad spectrum x-ray tube.

A detector array 112 subtends an angular arc opposite the examination region 106 relative to the radiation source 108. The detector array 112 detects radiation that traverses the examination region 106 and generates projection data indicative thereof. Where the radiation source voltage is switched between at least two emission voltages and/or two or more x-ray tubes emit radiation at two different emission voltages, the detector array 112 generates projection data for each of the radiation source voltages. For a single broad spectrum x-ray tube, the detector array 112 includes an energy-resolving detector (e.g., multi-layered, photon counting, etc.) that produces spectral projection data.

A reconstructor 114 reconstructs the projection data. This may include decomposing the projection data into various energy dependent components. Generally, with two attenuation values acquired simultaneously at two different photon energies, the photoelectric and Compton components can be derived. Because any two linearly independent sums of two bases functions span the entire attenuation coefficient space, a material, such as Iodine, can be represented by a linear combination of two basis materials (e.g., Iodine and water or a material, which is orthogonal to Iodine).

An example of a suitable decomposition approach is described in U.S. Pat. No. 8,442,184 B2, filed on Jun. 1, 2009, and entitled "Spectral CT," which is incorporated in its entirety herein by reference. Other approaches are also contemplated herein. The reconstructor 114 can reconstruct one or more of the energy dependent components, generating one or more images corresponding to one or more different energies, and/or combine the energy dependent components and generate non-spectral (or conventional) image data over the entire energy spectrum.

A computing system 122 includes at least one processor 124 (e.g., a microprocessor, a central processing unit, etc.) that executes at least one computer readable instruction stored in computer readable storage medium ("memory") 126, which excludes transitory medium and includes physical memory and/or other non-transitory medium. The microprocessor 124 may also execute one or more computer readable instructions carried by a carrier wave, a signal or other transitory medium. The computing system 122 further includes an output device(s) 128 such as a display monitor, a filmer, etc., and an input device(s) 130 such as a mouse, keyboard, etc.

The at least one computer readable instruction includes a contrast agent concentration simulation module 132. As described in greater detail below, the contrast agent concentration simulation module 132, in one instance, generates, from projection data and/or the image data of an already performed contrast enhanced scan, a simulated or "virtual" image corresponding to an image that would have been generated were the scan performed with a different (lower or higher) contrast agent dose, including no contrast. The resulting simulated or "virtual" image allows a clinician to visually observe how, for example, a lower contrast agent dose would affect the image quality of a subsequent scan. As such, a clinician can be assured ahead of time of obtaining an image quality level of interest (e.g., sufficient visibility of the vascular anatomy or contrast agent uptake in the tissue.) while reducing contrast agent exposure to a patient, which may mitigate adverse side effects of contrast agent to the patient.

In the illustrated embodiment, the imaging system 100 and the computing system 122 are shown as separate devices. In a variation, the computing system 122 can be part of the console 118 of the imaging system 100. In another variation, the contrast agent concentration simulation module 132 can be distributed across different systems, including one or more local system and/or one or more remote systems. In another variation, the contrast agent concentration simulation module 132 can be part of a web and/or cloud based service. Such a service can be a subscription based fee or free service.

The illustrated computing system 122 processes projection and/or image data obtained from the imaging system 100. In a variation, the projection and/or image data is obtained from a different imaging system and/or a data repository such as a picture archiving and communication system (PACS), a radiology information system (RIS), a hospital information system (HIS), an electronic medical record (EMR), a database, a server, an imaging system, a computer and/or other data repository. The data can be transferred via Digital Imaging and Communications in Medicine (DICOM), Health Level 7 (HL7), and/or other protocols.

Figure 2:
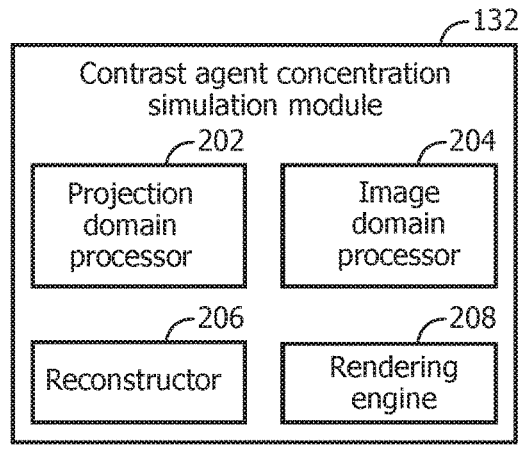

FIG. 2 schematically illustrates an example of the contrast agent concentration simulation module 132. In this example, the contrast agent concentration simulation module 132 includes a projection domain processor 202 and/or an image domain processor 204, a reconstructor 206, and a rendering engine 208.

The projection domain processor 202 processes projections in the projection domain, including reducing the overall contrast agent concentration of the projections, relative to the contrast agent dose administered for the scan, generating a set of simulated or lower dose projections.

The image domain processor 204 processes a reconstructed image in the image domain, including reducing the overall contrast agent concentration of each voxel, relative to the contrast agent dose administered for the scan, generating a simulated or "virtual" image, which is forward projected to produce a set of simulated or "virtual" projections.

The reconstructor 206 reconstructs the set of simulated or "virtual" projections, generating reconstructed image data with a contrast agent dose level modified from that of the scan. The rendering engine 208 visually displays the modified contrast agent image via an output device 128, such as a display monitor.

Figure 3:
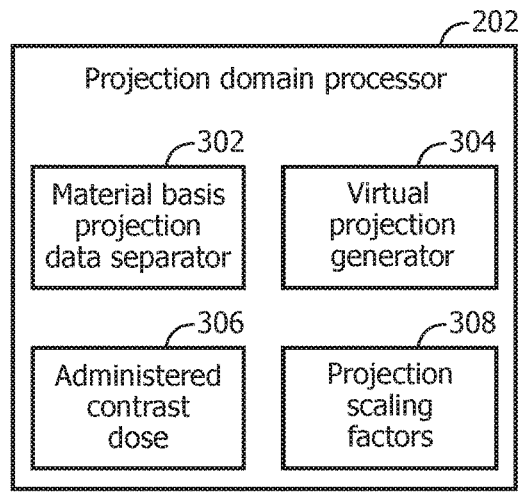

FIG. 3 shows an example of the projection domain processor 202.

The projection domain processor 202 includes a material basis projection data separator 302. The material basis projection data separator 302 decomposes the projections into at least contrast agent (e.g., iodine) only projections and non-contrast agent only projections.

The projection domain processor 202 further includes a virtual projection generator 304. The virtual projection generator 304 generates virtual projections with a contrast agent dose lower than an administered contrast agent dose 306.

In one instance, this includes down-weighting or scaling down the amount of contrast agent of each projection by a corresponding scaling factor. The scaling factor can be linear and/or otherwise, and can reduce the concentration of the contrast agent down to no contrast agent.

The amount of the reduction is determined through a set of projection scaling factors 308, which can include a default, a user specified, and/or other scaling factor. This includes a scaling based on a pre-defined percentage (e.g., 0%, 50%, etc.), a pre-defined concentration (e.g., in milligrams per liter), and/or otherwise.

The reconstructor 206 (FIG. 2) reconstructs the processed projection data. This may include reconstructing only the modified contrast agent only projections, the modified and other projections, only the original (non-modified) contrast agent only projections, and/or all of the original (non-modified) projections.

Figure 4:
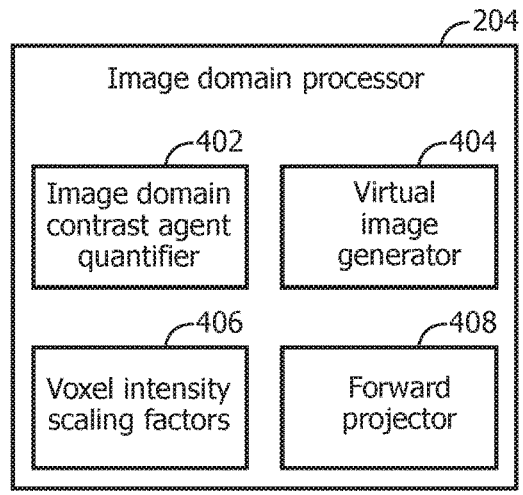

FIG. 4 shows an example of the image domain processor 204.

The image domain processor 204 includes an image domain contrast agent quantifier 402. The image domain contrast agent quantifier 402 quantifies an amount of contrast agent in each voxel of the contrast agent image.

The image domain processor 204 further includes a virtual image generator 404. The virtual image generator 404 generates a simulated or "virtual" image with a contrast agent dose lower than that determined to be in the contrast agent image.

In one instance, this includes down-weighting or scaling down the amount of contrast agent of each voxel by a corresponding scaling factor. The scaling factor can be linear and/or otherwise, and can reduce the concentration of the contrast agent down to no contrast agent.

The amount of the reduction is determined through a set of voxel intensity scaling factors 406, which can include a default, a user specified, and/or other scaling factor. Likewise, this includes a scaling based on a pre-defined percentage (e.g., 0%, 50%, etc.), a pre-defined concentration (e.g., in milligrams per liter), and/or otherwise.

The image domain processor 204 further includes a forward projector 408. The forward projector 408 forward projects the contrast agent modified image and/or a combination of the contrast agent modified image and one or more other images, producing corresponding contrast agent concentration modified projection data.

The reconstructor 206 (FIG. 2) reconstructs the processed projection data. This may include reconstructing only the projections corresponding to the contrast agent modified image, the projections corresponding to the combination of the contrast agent modified image and another image, and/or only the projections corresponding to the original contrast agent image.

Variations are discussed.

In a variation, to mitigate loss of resolution, the forward projected original (non-modified) projection data and the forward projected modified projection data can be subtracted or a difference there between can be added to the original projection data.

In another variation, the forward projection is used in an iterative reconstruction algorithm, optionally augmented by a simulation of photon and electronic noise to provide a more realistic image with respect to noise.

In another variation, the performance of another contrast agent is evaluated by replacing attenuation and/or other physical parameters (e.g., an absorption spectrum for energy resolving detectors) of the contrast agent.

In another variation, the tube current and/or voltage can additionally be changed.

In another variation, the contrast agent concentration only in a region of interest is changed.

In another variation, the reduction in contrast agent concentration is used in connection with a subsequent scan of a different patient in which the body mass index (BMI) and/or other information about the different patient is used to adjust the contrast agent concentration.

With a conventional (non-spectral) CT scanner, a region of interest (e.g., a vessel) is segmented (e.g., automatically, semi-automatically, and/or manually) from the image data, and an amount of contrast agent induced attenuation (or concentration) is approximately determine via calibration tables based on the measured attenuation, attenuation of blood or surrounding tissue without contrast.

Figure 5:
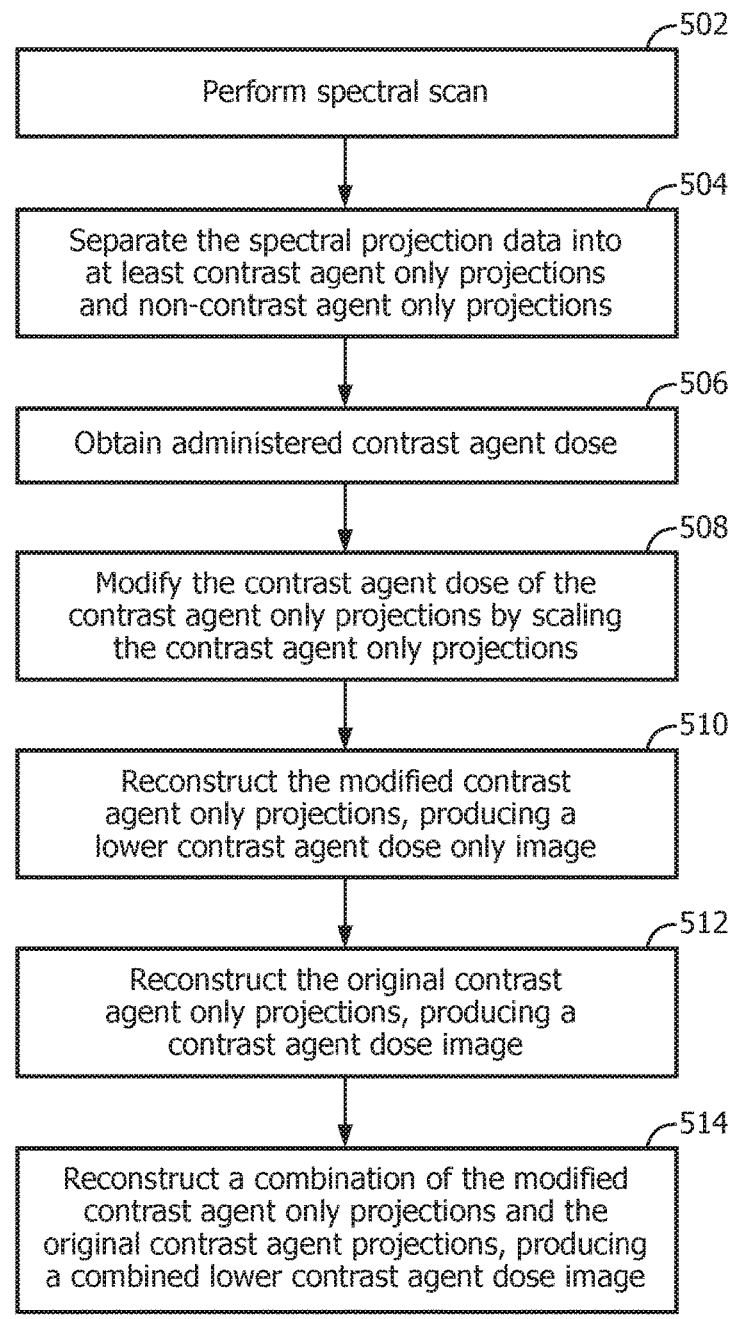
FIG. 5 illustrates an example method for simulating reduced contrast agent images in the projection domain.

FIG. 5 illustrates an example method for simulating a reduced contrast agent image in the projection domain.

It is to be appreciated that the ordering of the acts is not limiting. As such, other orderings are contemplated herein. In addition, one or more acts may be omitted and/or one or more additional acts may be included.

At 502, a spectral scan is performed, generating spectral projection data, which includes a set of energy dependent projections.

At 504, the spectral projection data is separated into at least contrast agent only projections and non-contrast agent only projections.

At 506, the administered contrast agent dose is obtained.

At 508, the contrast agent dose of the contrast agent only projections is modified, for example, through linear scaling based on a predetermined projection scaling function.

At 510, the modified contrast agent projections are reconstructed, producing a modified contrast agent image.

At 512, optionally, the original contrast agent projections are reconstructed to produce a contrast agent image.

At 514, optionally, the modified contrast agent projections and the original non-contrast agent projections are combined and reconstructed to produce a conventional (non-contrast agent) image.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

Figure 6:
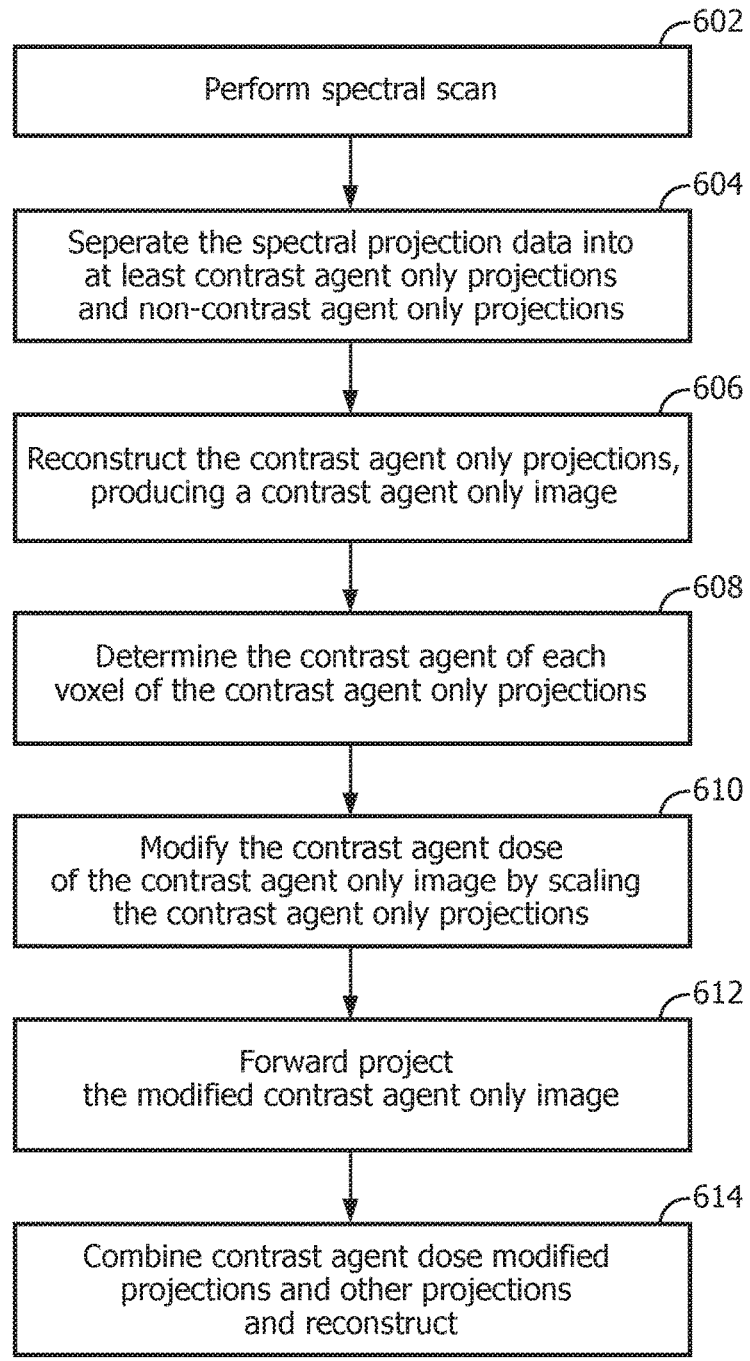
FIG. 6 illustrates an example method for simulating reduced contrast agent images in the image domain.

FIG. 6 illustrates an example method for simulating a reduced contrast agent image in the image domain.

It is to be appreciated that the ordering of the acts is not limiting. As such, other orderings are contemplated herein. In addition, one or more acts may be omitted and/or one or more additional acts may be included.

At 602, a spectral scan is performed, generating spectral projection data, which includes a set of energy dependent projections.

At 604, the spectral projection data is separated into at least contrast agent only projections and non-contrast agent only projections.

At 606, the contrast agent projections are reconstructed, producing a contrast agent only image.

At 608, the contrast agent dose of each voxel in the contrast agent only image is determined.

At 610, the contrast agent dose of each voxel of the contrast agent only image is modified, for example, through linear scaling based on a predetermined voxel intensity scaling function.

At 612, the contrast agent dose modified image is forward projected, producing contrast agent dose modified projections. Optionally, the contrast agent dose modified image can first be combined with a non-contrast and/or other image.

At 614, optionally, the contrast agent dose modified projections and the non-contrast projections are combined and reconstructed to produce a produce a conventional (non-contrast agent) image.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

Figure 7:
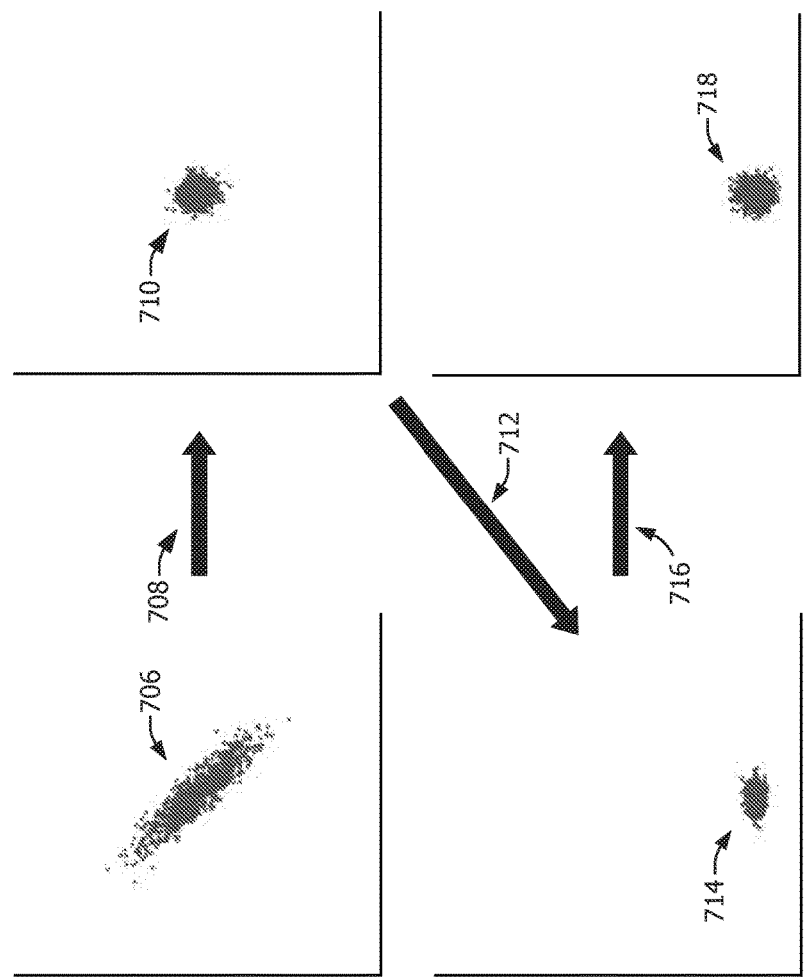
FIG. 7 shows an example scatter plot in connection performing anti-correlated filtering and noise modification.

Reducing the amount of contrast changes the overall absorption along the line integrals, which reduces the noise in the image data. The following describes a non-limiting example of how to add back an appropriate amount of noise, in connection with scatter plots shown in FIG. 7. In FIG. 7, a y-axis 702 represents the contrast only projection data, and the x-axis 704 represents the non-contrast only projection data.

At the point of decomposition into contrast only projection data and non-contrast projection data, variances and covariance of the projection data are determined. As shown in FIG. 7, the correlated noise leads to an elongated distribution 706 of samples in the scatter plot. Anti-correlated filtering is then applied to the projection data at 708. In one instance, the filtering filters out only correlated noise such that after the filtering, the contrast only data and the non-contrast data have only uncorrelated noise. This is shown in the scatter plot at 710. The noise distribution should now be roughly a separable 2D Gaussian without correlation). The noise variance in the contrast projection data is Var(C).

The contrast content can then be scaled down by a factor f (e.g., f=¼) at 710. As a side effect, the noise is also scaled down. To compensate for this scaling of the noise, the noise variance of the contrast projection data is scaled by a factor $f^2$ so the noise variance of the contrast projection data is now $f^2$ Var(C) as shown in the scatter plot at 712. The original noise is then recovered by adding Gaussian white noise with zero mean and variance $(1-f^2)$ Var(C) at 716, producing the scatter plot shown at 718. Other approaches for adding noise back are also contemplated herein.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
    obtaining a set of energy dependent data generated from a spectral scan, wherein the set of energy dependent data includes a sub-set of data corresponding to only contrast agent;
    separating the sub-set of data from other data of the energy dependent data, wherein the other data includes non-contrast agent data;
    scaling the sub-set of data to change a concentration of the contrast agent in the sub-set of data from that of the sub-set of data;
    visually presenting at least the scaled sub-set of data;
    wherein the set of energy dependent data is projection data, and the sub-set of data corresponding to only contrast agent includes contrast agent only projections;
    obtaining an administered amount of the concentration; and
    linearly scaling the contrast agent only projections by a scaling factor, thereby reducing an amount of contrast agent in the contrast agent only projections.

2. The method of claim 1, further comprising:
    visually presenting the sub-set of data.

3. The method of claim 1, further comprising:
    combining the at least scaled sub-set of data and the other data of the energy dependent data, producing contrast agent modified data; and
    visually presenting the contrast agent modified data.

4. The method of claim 1, further comprising:
    combining the sub-set of data and the other data of the energy dependent data; and
    visually presenting the combined data.

5. The method of claim 1, wherein the scaling factor is based on one of a percentage of the administered amount or a predetermined quantity.

6. The method of claim 1, further comprising:
    reconstructing the scaled contrast agent only projections, generating a modified contrast agent only image.

7. The method of claim 1, further comprising:
    combining the scaled contrast agent only projections and the non-contrast agent projections; and
    reconstructing the combined projections, generating a modified contrast enhanced image.

8. A method, comprising:
    obtaining a set of energy dependent data generated from a spectral scan, wherein the set of energy dependent data includes a sub-set of data corresponding to only contrast agent;
    separating the sub-set of data from other data of the energy dependent data, wherein the other data includes non-contrast agent data;
    scaling the sub-set of data to change a concentration of the contrast agent in the sub-set of data from that of the sub-set of data;
    visually presenting at least the scaled sub-set of data;
    determining a contrast agent concentration of each voxel in the image;
    linearly scaling each voxel of the contrast agent only image by a scaling factor, thereby reducing an amount of contrast agent in the contrast agent only image; and
    wherein the set of energy dependent data is image data, and the sub-set of data corresponding to only contrast agent includes contrast agent only image.

9. The method of claim 8, wherein the scaling factor is based on one of a percentage of the administered amount or a predetermined quantity.

10. The method of claim 8, further comprising:
    forward projecting the scaled contrast agent only image, producing scaled contrast agent only projections;
    combining the forward projected data with non-contrast agent projections; and
    reconstructing the combined projections, generating a modified contrast enhanced image.

11. A computing system, comprising:
    a memory that stores instructions of a contrast agent concentration simulation module;
    a processor that receives a set of energy dependent data, including a first sub-set of data corresponding to only contrast agent and second sub-set of data corresponding to only non-contrast agent; extracts the first sub-set of data corresponding to only contrast agent; changes a concentration of the contrast agent in the extracted first sub-set of data corresponding to only contrast agent; and visually presents at least the changed concentration sub-set of data; and
    wherein the first sub-set of data is projection data, and the processor applies a scaling factor to each projection of the first sub-set of data.
    wherein the processor reconstructs the scaled first sub-set of data, thereby generating a reduced contrast agent concentration image, and visually presents the reduced contrast agent only concentration image.

12. A computing system, comprising:
    a memory that stores instructions of a contrast agent concentration simulation module;

a processor that receives a set of energy dependent data, including a first sub-set of data corresponding to only contrast agent and second sub-set of data corresponding to only non-contrast agent; extracts the first sub-set of data corresponding to only contrast agent; changes a concentration of the contrast agent in the extracted first sub-set of data corresponding to only contrast agent; and visually presents at least the changed concentration sub-set of data; and wherein the processor reconstructs the scaled first sub-set of data, thereby generating a reduced contrast agent concentration image, and visually presents the reduced contrast agent only concentration image; and wherein the processor combines the scaled first sub-set of data and the second sub-set of data, and reconstructs the combined data, thereby generating a reduced contrast enhanced combined image, and visually presents the reduced contrast enhanced combined image.

13. The computing system of claim 11, wherein the first sub-set of data is image data, and the processor applies a scaling factor to each voxel of the first sub-set of data.

14. The computing system of claim 11, wherein the processor adds noise back to the projection data by:
determining variances and a covariance for the first sub-set of only contrast agent data and the second sub-set of only non-contrast agent data;
applying anti-correlated filtering to the first sub-set of only contrast agent data and the second sub-set of only non-contrast agent data, which filters out correlated noise, generating first sub-set of only contrast agent data and the second sub-set of only non-contrast agent data having only uncorrelated noise;
scaling down a contrast content in the first sub-set of only contrast agent data having only uncorrelated noise by a predetermined factor;
scaling up the noise content in the contrast content scaled down first sub-set of only contrast agent data having only uncorrelated noise data by a square of the predetermined factor; and
adding Gaussian white noise to recover the original noise.

15. A computer readable storage medium encoded with computer readable instructions, which, when executed by a processor, cause the processor to:
generate a virtual image with a contrast agent concentration that is less than an administered contrast agent concentration based on scan data from a scan with the administered contrast agent concentration;
visually display the virtual image with the contrast agent concentration that is less than the administered contrast agent concentration;
generate an image for the administered contrast agent concentration; and
replace voxel values of the scan data with voxel values for a different contrast agent concentration, creating a contrast agent modified image, wherein the scan data is reconstructed image data; and
visually display the contrast agent modified image; and
wherein the computer readable instructions, when executed by the processor, further cause the processor to:
generate, from the contrast agent modified image, a second virtual image with a reduced contrast agent concentration for the different contrast agent; and
visually display the second virtual image with the reduced contrast agent for the different contrast agent.

16. The computer readable storage medium of claim 15, wherein the computer readable instructions, when executed by the processor, further cause the processor to:
generate an image for the administered contrast agent concentration from the scan data; and
visually display the image.

17. The computer readable storage medium of claim 15, wherein the computer readable instructions, when executed by the processor, further cause the processor to:
replace attenuation values of the scan data with values for a different contrast agent concentration, creating contrast agent modified projection data, wherein the scan data is projection data;
reconstruct the contrast agent modified projection data, creating a contrast agent modified image; and
visually display the contrast agent modified image.

18. A computer readable storage medium encoded with computer readable instructions, which, when executed by a processor, cause the processor to:
generate a virtual image with a contrast agent concentration that is less than an administered contrast agent concentration based on scan data from a scan with the administered contrast agent concentration;
visually display the virtual image with the contrast agent concentration that is less than the administered contrast agent concentration; and
wherein the computer readable instructions, when executed by the processor, further cause the processor to:
Generate, from the contrast agent modified image, a second virtual image with a reduced contrast agent concentration for the different contrast agent; and
visually display the second virtual image with the reduced contrast agent for the different contrast agent.

19. The computer readable storage medium of claim 16, wherein the computer readable instructions, when executed by the processor, further cause the processor to:
generate an image for the administered contrast agent concentration from the scan data;
generate, for a user identified sub-portion of the image, virtual voxels with the contrast agent concentration that is less than the administered contrast agent concentration, creating a modified image; and
visually display the modified image.

* * * * *